US006632632B1

United States Patent
Lorentzen et al.

(10) Patent No.: US 6,632,632 B1
(45) Date of Patent: Oct. 14, 2003

(54) RAPID METHOD OF DETECTION AND ENUMERATION OF SULFIDE-PRODUCING BACTERIA IN FOOD PRODUCTS

(75) Inventors: Grete Lorentzen, Oslo (NO); Olaug Taran Skjerdal, Oslo (NO); James D. Berg, Jar (NO)

(73) Assignee: Colifast AS

( * ) Notice: Subject to any disclaimer, the term of this patent is extended or adjusted under 35 U.S.C. 154(b) by 0 days.

(21) Appl. No.: 10/016,854

(22) Filed: Dec. 14, 2001

(51) Int. Cl.[7] .............................. C12Q 1/04; C12Q 1/00; C12Q 1/22; C12Q 1/02
(52) U.S. Cl. .............................. 435/34; 435/4; 435/31; 435/29; 435/968; 426/231
(58) Field of Search ................................ 435/34, 4, 31, 435/29, 968; 426/231

(56) References Cited

U.S. PATENT DOCUMENTS

| | | | |
|---|---|---|---|
| 4,058,621 A | 11/1977 | Hill | 424/295 |
| 5,620,865 A | 4/1997 | Chen et al. | 435/34 |
| 5,976,827 A * | 11/1999 | Jeffrey et al. | 435/34 |
| 6,197,577 B1 * | 3/2001 | Jeffrey et al. | 435/288.7 |

OTHER PUBLICATIONS

Gram et al., "Detection of Specific Spoilage Bacteria from Fish Stored at Low (0°C) and High 0°C) Temperatures", International Journal of Food Microbiology, 4 (1987) 65–72.
"Bacteriological Examination of Fresh and Frozen Seafood", Nordic Committee on Food Analysis, No. 96, 2nd Edition, 9 pages, (1994).

Jangi et al., "Development of a Simple Test for the Bacteriological Quality of Drinking Water and Water Classification", IV. Hydrogen Sulphide Production as a Bacteriological Water Quality Indicator, IDRC, http://www.idrc.ca/library/document/053714/, 20 pages, (1997).
"An Easy and Cost Effective Method to Test Water in Rural Areas", Water Research Commission, P.O. Box 824, Pretoria, 0001 South Africa, http://www.wrc.org.za/wrcpress/ruralwater.htm, 1 page, (2001).
PCT/US02/37675, PCT International Search Report, Mar. 26, 2003, 3 pages.

* cited by examiner

Primary Examiner—Louise N. Leary
(74) Attorney, Agent, or Firm—Dunlap, Codding & Rogers, P.C.

(57) ABSTRACT

A rapid method for detecting spoilage of a food sample, particularly a fish sample, by detecting and enumerating sulfide-producing bacteria (SPB). A growth medium containing iron and sulfur is combined with the food sample forming an incubation mixture which is incubated for a period of time. A plurality of fluorescence measurements are taken during an incubation period of about 4 hours to 17 hours at 30° C. SPB are determined to be present in the sample if the fluorescence measurement initially increases and then decreases to form a fluorescence maximum (peak). The time to detection of the fluorescence peak can be used with a correlation schedule to enumerate the SPB in the food sample. A visual test can also be used to identify color changes in the incubation mixture to provide a semi-quantitative enumeration of SPB effective in about 4 hours to 17 hours at 30° C.

36 Claims, 4 Drawing Sheets

(1 of 4 Drawing Sheet(s) Filed in Color)

Color Chart for
Visual Detection

RAPID METHOD OF DETECTION AND ENUMERATION OF SULFIDE-PRODUCING BACTERIA IN FOOD PRODUCTS

CROSS REFERENCE TO RELATED APPLICATION

Not Applicable

STATEMENT REGARDING FEDERALLY SPONSORED RESEARCH OR DEVELOPMENT

Not Applicable

BACKGROUND

The present invention relates to rapid methods for detection and quantification of microorganisms in food products for human consumption or use, and more particularly to rapid methods for the detection and quantification of sulfide-producing bacteria in fish products.

Among the most predominant bacteria associated with spoilage of fish products, and food products in general are sulfide-producing bacteria (SPB) such as *Shewanella putrefaciens*. SPB are especially responsible for spoilage of many kinds of foods such as seafood, including fish, fish products, mussels, mussel products, shellfish and shellfish products and other meat products such as poultry (e.g., chicken and turkey), pork, beef, and lamb, and even dairy products such as cheese. SPB are particularly responsible for spoilage in fresh or cooled aerobically-packed seafood. These bacteria are present in seawater and on the surface of all living fish and shellfish, and are transferred to the flesh during catch and processing. They grow to high levels and cause spoilage even when the fish are stored on ice (at approximately 0–4° C.). The spoilage is mainly due to growth of psychrotropic bacteria, including *S. putrefaciens*.

Traditionally, microbial analysis of fish has been limited to total viable counts. Indicator testing for total viable organisms and coliforms are the most widely used tests for routine monitoring of microbial contamination. However, during the last decade, it has been discovered that the shelf life of fish and shellfish is correlated to the level of specific spoilage bacteria and not to the count of total viable organisms. Spoilage is sensory detectable when the number of sulfide producing bacteria exceeds $10^7$ colony forming units per gram (cfu/g) of fish muscle. In the case of cod from the North Atlantic, for example, this level is reached after approximately 12 days when the fish are stored on ice, after approximately 7 days of storage at 4° C., and after even shorter times when stored at higher temperatures. The growth of bacteria is exponential, and the shelf life of the fish can be predicted from the number of SPB in the fish, and the growth rate of these bacteria at the actual storage temperature. In addition to sulfide production, SPB contribute to the accumulation of trimethylamine (TMA) in the fish. TMA is a primary component of unpleasant fishy odors.

Traditional agar plate methods have been developed for analysis of *S. putrefaciens* and other SPB in fish (Gram et al., 1987). In those methods, a non-specific growth medium is supplemented with thiosulfate, cysteine and ferricitrate. Bacteria that are able to produce sulfide from thiosulfate or cysteine appear as black colonies on the agar, due to precipitation of ferrous sulfide. The detection is therefore directly related to the spoilage property of the bacteria. This is a benefit in analysis of spoilage bacteria, since the spoilage potential of the microbe is more important that its identity. However, the agar plate method has the same disadvantages as all other agar plate methods. For instance, it does not give the possibility for early warning and it requires laboratory facilities, including an autoclave and technicians skilled in sterile technique. The method is also time and labor intensive. Also, the lowest detection level is about 100 cfu/g, which is not adequate for presence/absence tests. Furthermore, the required analysis time is at least one to three days depending on the incubation temperature. Since the analysis takes so long, this method of analysis cannot be used to make a timely decision regarding whether or not fish should be purchased, sold, or used, or whether or not the fish can be used to produce other products. Therefore, more rapid methods of detection are desired to be able to expedite the decision-making process regarding how food products such as fish and shellfish which are contaminated with sulfide-producing bacteria can be used, sold, or purchased.

Other, more rapid, analyses based on bacterial growth with a possibility for early warning have been developed for total viable counts, for several hygienic indicator bacteria and for certain pathogens. For example, a sample is inoculated in a growth medium which is more or less specific for the bacterium that is going to be detected or quantified. The medium has an indicator that is a specific substrate for the desired bacterium. The product produced by turnover of this substrate becomes detectable (for example by fluorescence) when the number of microbes reaches a certain level. Other examples are impedimentary methods, where the indication is related to a change in the number of charged molecules. In these methods, the number of microbes in the sample is calculated indirectly based on the time required until detection and on the growth rate at the given conditions. However, all of these methods suffer from one or more deficiencies, and there continues to be a need for methods which will more rapidly detect and/or quantify SPB which cause product spoilage.

SUMMARY OF THE INVENTION

The present invention comprises methods for rapidly detecting and quantifying sulfide-producing bacteria, for instance *S. putrefaciens*, in a sample of a food product comprising meat, dairy or fish. The food sample is combined with a quantity of growth medium. The growth medium preferably comprises an iron compound (ferric citrate or ferrous sulfate, for example) and organic and/or inorganic sulfur compounds (cysteine and sodium thiosulfate, for example) and forms an iron precipitate (e.g., iron sulfide) when exposed to *S. putrefaciens* or other sulfide-producing bacteria. The growth medium and the sample forms an incubation mixture. The incubation mixture is incubated for a predetermined incubation period, for example from about four or five hours to 16–18 hours.

The level of SPB in the sample is determined by using a visual detection method to identify a color change, or by using fluorescence detection methods which detect trends in fluorescence production of the incubation mixtures which are correlated with SPB numbers.

BRIEF DESCRIPTION OF THE DRAWINGS

The file of this patent contains at least one drawing executed in color. Copies of this patent with color drawings will be provided by the Patent and Trademark Office upon request and payment of the necessary fee.

Figure 1:
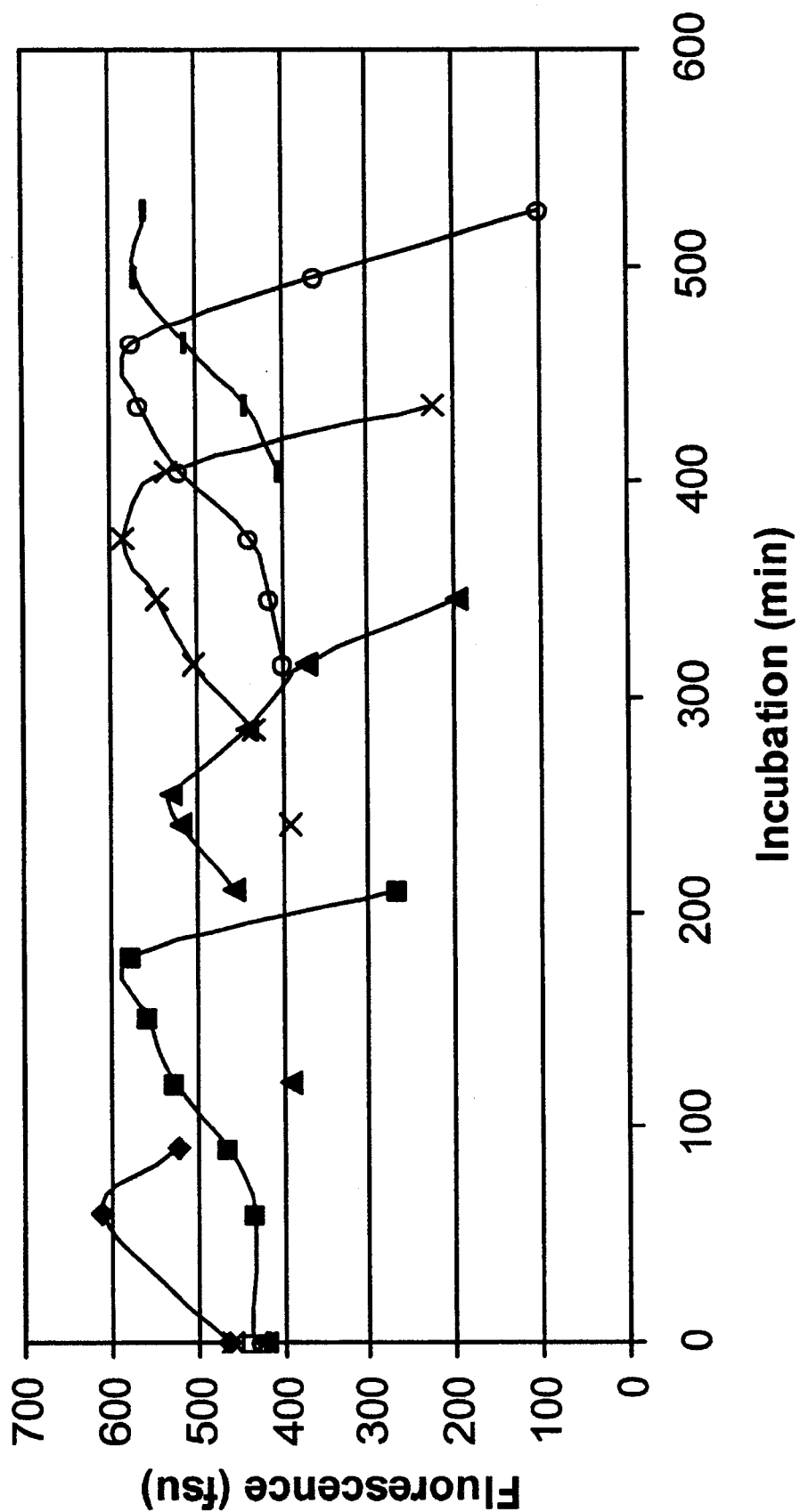
FIG. 1 is a graph depicting results for rapid enumeration of *S. putrefaciens* in pure cell culture, wherein sample 1 (♦)

has $3.9 \times 10^7$ cfu/ml of *S. putrefaciens*; sample 2 (■) has $9.7 \times 10^6$ cfu/ml of *S. putrefaciens*; sample 3 (▲) has $2.4 \times 10^6$ cfu/ml of *S. putrefaciens*; sample 4 (x) has $4.8 \times 10^4$ of *S. putrefaciens*; sample 5 (○) has $4.8 \times 10^3$ cfu/ml of *S. putrefaciens* and sample 6 (▄) has $3.8 \times 10^4$ cfu/ml of of *S. putrefaciens*.

Figure 2:
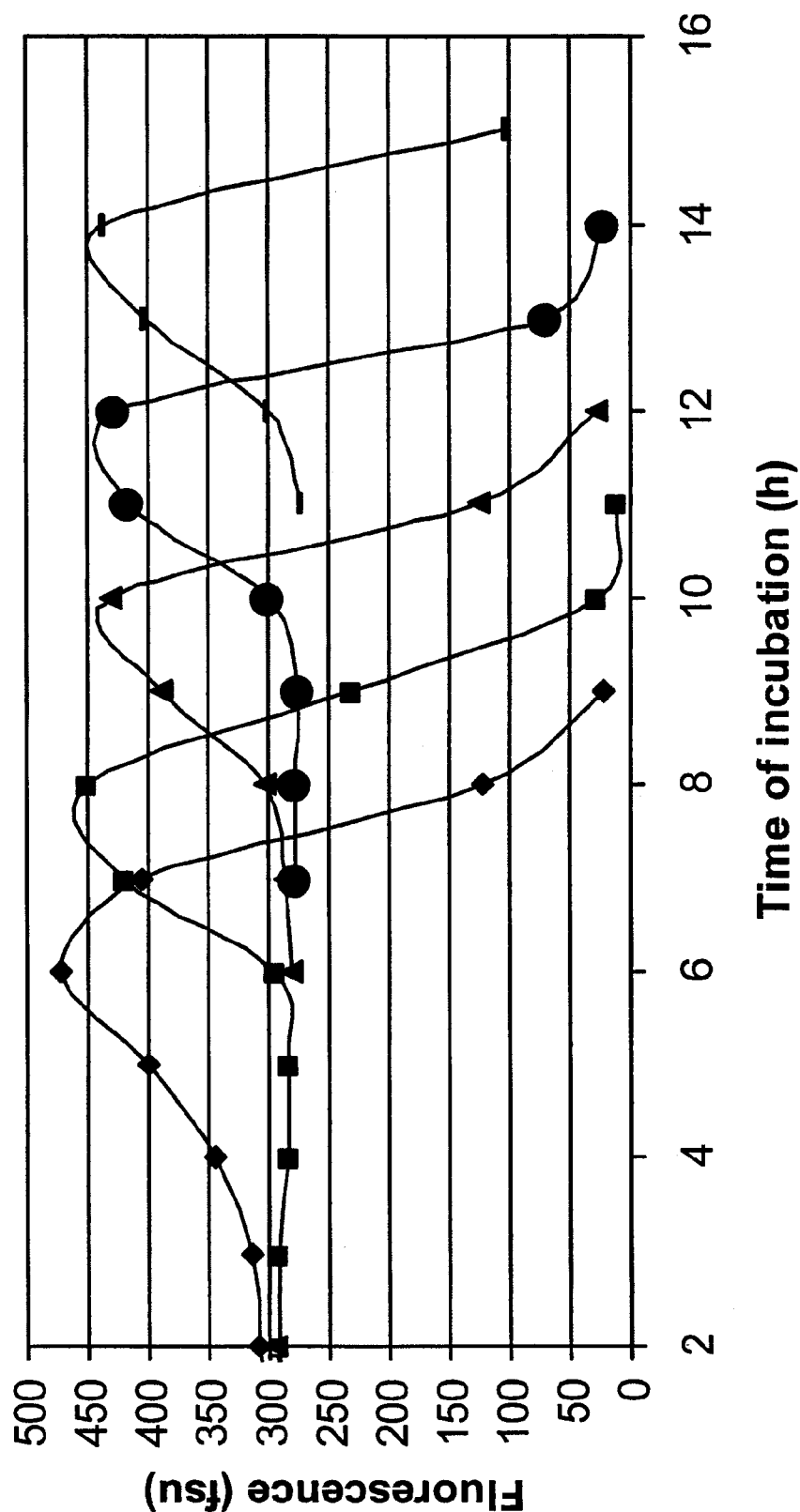

FIG. 2 is a graph showing the development of fluorescence in cod samples contaminated with *S. putrefaciens*, wherein sample 1 (♦) has $1.4 \times 10^5$ cfu/ml of *S. putrefaciens*; sample 2 (■) has $1.4 \times 10^4$ cfu/ml; sample 3 (▲) has $1.4 \times 10^1$ cfu/lm; sample 4 (●) has $1.4 \times 10^2$ cfu/ml; and sample 5 (▄) has $1.4 \times 10^1$ cfu/ml. The distance from the y-axis (start of the analysis) to the point where the fluorescence starts to increase is equal to the "time to detection" for *S. putrefaciens*.

Figure 3:
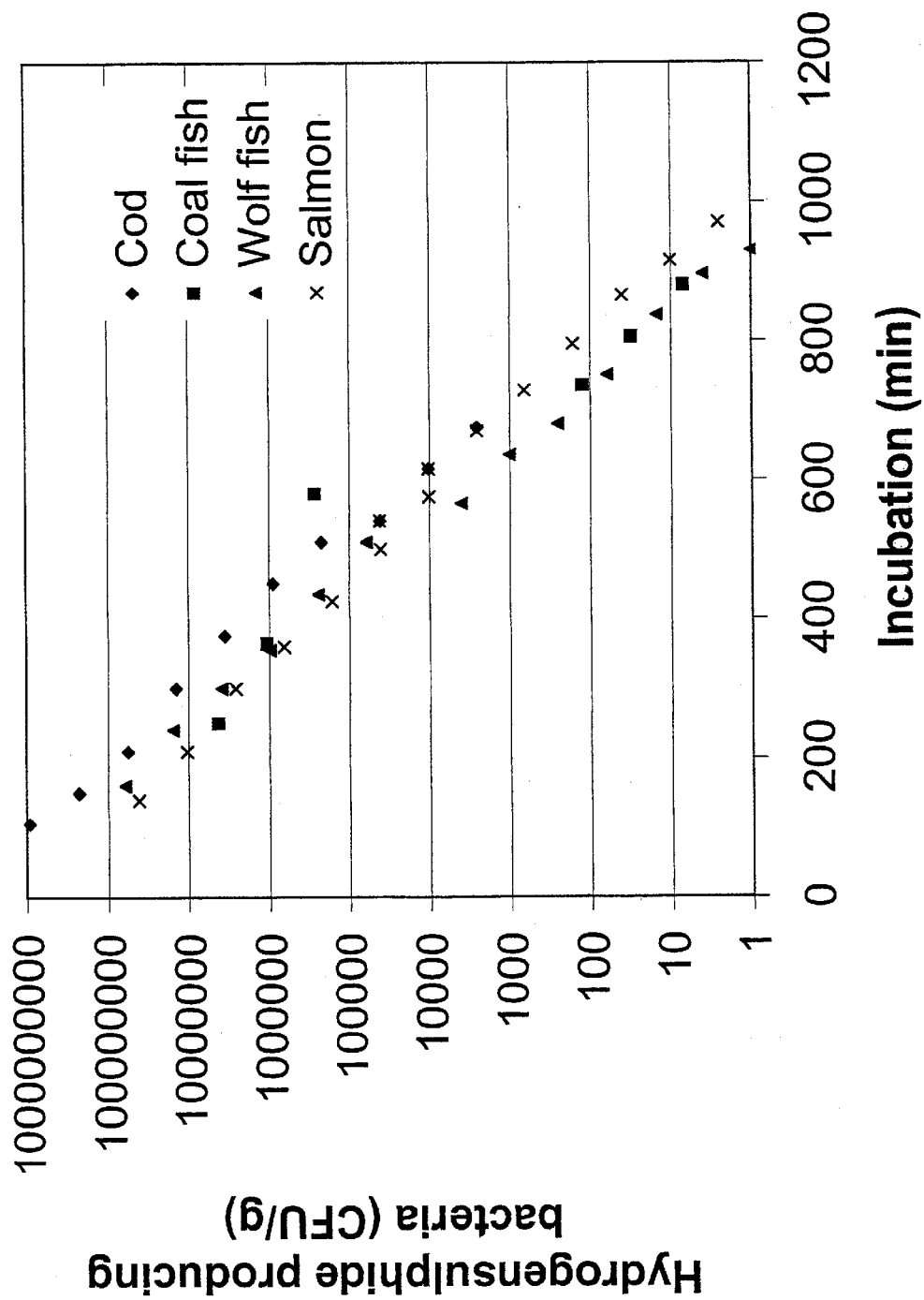

FIG. 3 is a graph depicting the correlation between the time of detection (x-axis) and the number of naturally-occuring sulfide-producing bacteria in fresh fish determined by the standard method (y-axis), wherein various fish species are represented as cod (♦) ($R^2=0.89$), coal fish (■) ($R^2=0.99$), salmon (x) ($R^2=0.99$), wolf fish (▲) ($R^2=0.99$), cultivated in IAL (Iron Agar Lyngby) broth and incubated at 30° C.

Figure 4:
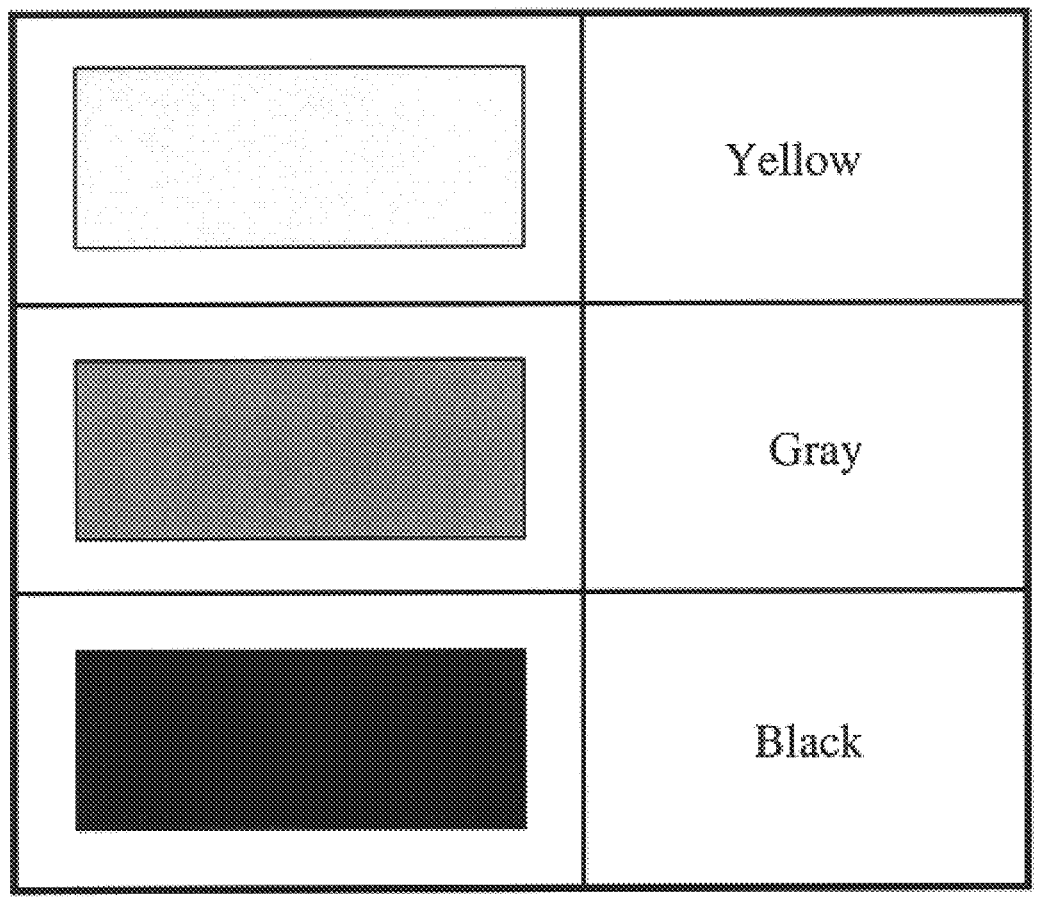

FIG. 4 is a color chart for assessing color of an incubation mixture after an incubation period.

DETAILED DESCRIPTION OF THE INVENTION

The present invention comprises a rapid method for quantification of sulfide-producing microbes, such as *Shewanella putrefaciens* in food products, including meat, or diary, and particularly in fish and shellfish. The method is based on the formation of iron sulfide by SPB in a liquid growth medium. Iron sulfide formation is detected as a change in the background fluorescence in the growth medium or as a color change in the medium from yellow to gray to black or as a blackening on the surface of an intact portion of the sample.

With the present invention it is possible to detect and enumerate even low numbers ($<10^4$ cfu/g) of sulfide-producing bacteria in samples of fresh fish (such as, but not limited to: cod (*Gadus morhua*), redfish (Norwegian haddock (*Sebastus marinus*)), salmon (*Salmo salar*), haddock (*Melanogrammus aegifinus*), coal fish (*Pollachius virens*) and wolf fish (*Anarhichas lupus*)) within, for example, 4, 5, 6, 7, 8, 9, 10, 11, 12, 13, 14, 15, 16 or 17 or increments there between hours, which is considered sufficiently rapid and timely to allow corrective actions (e.g., to prevent or suspend the processing, purchasing, or selling) in the case of unacceptable bacterial contamination in the food product. It also is possible to use the method as a "pass-fail" test for SPB at particular levels, when desired. The detection level is 1–5 bacteria per gram of sample, which is at least tenfold more sensitive than the detection level in the traditional agar plate method.

As bacteria start to grow and produce $H_2S$, the properties of the media change as ferricitrate (or ferrous sulfate) is reduced and iron sulfide, FeS, is formed. When $Fe^{3+}$ is reduced to $Fe^{2+}$, the emission fluorescence initially increases, then decreases due to the darkening of the sample mixture caused by an increase in the amount of the iron sulfide precipitate. This increase, then decrease, in fluorescence is expressed as a curve with a peak. Samples are read in fluorescent signal units (fsu), which is the relative intensity of the fluorescence emission from the samples. Samples of fish products are liquified and mixed with an iron broth growth medium forming an incubation mixture, and are incubated for an incubation period. The incubation mixture may be incubated, for example, at a temperature of 28° C.±0.5° C., 29° C.±0.5° C., 30° C. ±0.5° C., 31° C.±0.5° C., 32° C.±0.5° C., 33° C.±0.5° C., 34° C.±0.5° C., or 35° C. ±0.5° C.

Growth of SPB visibly alters the iron broth in two stages. In the first stage, the color of the iron broth changes from yellow to bright yellow (both transparent). In the second stage, iron sulfide precipitate (FeS) starts to form, causing the sample to become gray and eventually black (opaque). When measured with the fluorometer, the first visible stage (yellow) is expressed as an increase in fluorescence signal units and the second visible stage (gray) is expressed as a reduction of fluorescence signal units. The time at which a fluorescence peak occurs represents the "time to detection" of SPB of the sample. The quantity of SPB is related to the concentration of FeS. When the concentration of FeS in the incubation mixture reaches a particular level, the fluorescent light emitted is reduced and the fluorescence begins to decrease, the fluorescence peak having been achieved. Fluorescence is measured at regular intervals, for example, every half-hour or hour. Typically, at least three fluorescence measurements are necessary to identify when the fluorescence peak occurs.

Briefly, the methods described herein are carried out by mixing a "stomached" sample of a food product with peptone water. A sample of the peptone water mixture is added to a growth medium (iron broth media) to make an incubation mixture and incubating the incubation mixture at a predetermined temperature (e.g. 30° C). The results (SPB concentration of the food product) are determined by (1) detecting a visible color change in the mixture from yellow to gray, (2) manually taking a series of fluorescence measurements of the incubation mixture, including during the visible color change from yellow to gray, or (3) automatically taking a series of fluorescence measurements during the course of incubation of the sample. The conventional method for detection and enumeration of sulfide-producing bacteria can be performed as a reference if desired.

METHODS

Iron Broth Media

Iron agar Lyngby (IAL) is a conventional growth medium used in the determination of total viable counts (TVC) of $H_2S$—producing organisms and is made by combining 2% peptone (Difco); 0.3% Lab Lemco powder (Oxoid); 0.3% yeast extract (Difco); 0.03% ferric-citrate (Merck); 0.03% sodium thiosulfate (Merck); 0.5% NaCl (Merck); and 1.2% agar (Difco) dissolved in 1000 ml distilled water. The pH is then adjusted to 8.2. To dissolve the ferric-citrate completely, sterilization of the medium at 121° C. for 15 minutes is required, obtaining a pH of 7.4±0.2. After sterilization, sterile-filtered L-cysteine; 0,04% (Sigma) is added.

In an alternate version of the iron broth medium, ferrous sulfate ($Fe^{3+}$) could be substituted for ferric citrate ($Fe^{2+}$) at the same concentration (0.03%). The alternate medium enables a color change from yellow to gray which is detectable earlier due to a more prominent blackening of the medium.

For the methods of rapid detection of sulfide-producing bacteria described herein, the samples are cultivated in iron broth (IAL media minus agar) rather than Iron Agar Lyngby. Peptone water is used for dilution of samples and is formed by dissolving 8.5 gm NaCl (Difco) and 1 gm peptone (Difco) in 1000 ml of water. The peptone water is then sterilized at 121° C. for 15 min.

Preparation of Meat Sample

A sample of meat or fish (10 g) is homogenized in 30 ml of peptone water in a stomacher filterbag (Seward, model 400 6041/str) using a stomacher (Lab Blender 400). Required time in the stomacher is approximately 4 minutes or until the sample is homogenized. A subsample of 1.5 ml of the stomached sample is dispensed from the filterbag and added to a sterile tube containing 4.5 ml of iron broth as described further herein. The tube is capped and mixed.

As noted, elsewhere herein the sample of the food product may comprise, for example, fish, shellfish, cheese, poultry, beef, pork, lamb, or other fish, meat or dairy products.

Fluorescence Measurement

In a preferred embodiment of the present invention, a laboratory fluorometer is used to detect SPB. In this embodiment, a fluorometer such as a TURNER DESIGNS TD-700 fluorometer can be used. The TD-700 has two optical filters: an excitation filter with a 380 nm narrow band pass, and an emission filter with a 450 nm narrow band pass. The TD-700 is single point calibrated using pure iron broth media for setting the optimal sensitivity and range for the fluorometer. Pure iron broth media is set to 400 fluorescence units (fsu). Fluorescence measurements in this embodiment preferably are taken each 15–30 minutes and preferably are incubated at 30° C. In another embodiment, fluorescence is automatically measured using a COLIFAST CA-100.

Standard Fluorescence Curve

To prepare a standard curve for use in the fluorescence test, *S. putrefaciens* can be grown overnight in iron broth at 20° C. After this pre-enrichment step, serial 10-fold dilutions are made using peptone water. A sample of the peptone water is transferred to iron broth and mixed. From each dilution of the iron broth mixture, two parallel samples of 3 ml are transferred to two cuvettes. The samples are preferably incubated in the open cuvettes at 30° C. Before using the fluorometer to measure fluorescence, the cuvette is capped and mixed by inversion in order to obtain a homogenous sample. The fluorescence is generally measured at room temperature (18° C.–20° C.).

EXAMPLES

Referring now to FIG. 1, the results for rapid enumeration of *S.putrefaciens* in pure cell culture cultivated in iron broth are shown. FIG. 1 shows the relationship between fluorescence and concentration of bacteria with regard to the time of detection. When bacterial concentrations are initially high, the "time to detection" (TTD) or "detection time" is very early in the incubation period, whereas, when initial concentration is low, "time to detection" is much later in the incubation period.

Referring to FIG. 2, the graph shows the development of fluorescence in samples of cod contaminated with varying levels of *S.putrefaciens*. The samples are cultivated in iron broth and incubated at 30° C. As bacteria increase in each sample, there is an increase in fluorescence over a period of time which is indicated by the upward curve in the graph. When the fluorescence begins to decrease as more iron sulfide is formed, a peak has been formed. In FIG. 2, the cod sample having about $10^4$ cfu/g of *S. putrefaciens* attains a fluorescence peak (i.e. time to detection) in about 8 hours, for example.

Referring now to FIG. 3, the graph therein shows the correlation between the time to detection and the number of sulfide-producing bacteria in samples of several fish species. As shown in FIG. 3, there is a strong negative correlation (high $R^2$) between the number of sulfide-producing bacteria in a sample, and the time necessary to detect the bacteria in a sample of contaminated food, fish or meat, where time to detection is defined as the time required to achieve maximum (peak) fluorescence.

Though not wishing to be constrained by theory, it is suspected that the increase in fluorescence can be explained by the decrease in the concentration of $Fe^{3+}$ in the broth due to the formation of $Fe^{2+}$. When a specific concentration of sulfide-producing bacteria is reached in the medium, the fluorescence decreases. This is visually observed as a conversion from yellow to a gray color in the incubation mixture which eventually turns black due to FeS formation. The detection time (the x-axis in FIG. 3) is defined as the distance from the y-axis (start of analysis) to the point of maximum (peak) fluorescence.

In the invention contemplated herein, a method of detecting and enumerating SPB in a food sample, as defined elsewhere herein, includes preparing the food sample, for example a fish sample as a liquified food sample. Fish or shellfish, for example may be selected from the group comprising fish (including cod, coal fish, wolf fish, red fish, haddock, and salmon), molluscs, marine animals, crustaceans, or any product derived therefrom. An incubation mixture is formed by combining the liquified food sample with a growth medium comprising an iron compound and a sulfur compound. An iron precipitate is formed in the incubation mixture when SPB act upon the iron compound and sulfur compound in the growth medium. The incubation mixture is incubated at an incubation temperature for an incubation period. The incubation temperature of the method is preferably from about 28° C.±0.5° C. to about 35° C.±0.5° C. and more preferably about 30° C.±0.5° C. The incubation period is generally from about 4 to about 17 hours and may be any incremental time period therein. A plurality of fluorescence measurements (usually at least three) are taken from the incubation mixture during the incubation period. It is concluded that the food sample contains a particular quantity of SPB when the fluorescence measurements taken from the incubation mixture show a maximum fluorescence. The measurements indicate a fluorescence peak in the incubation mixture during the incubation period (an increase followed by a decrease).

Enumeration of SPB by Fluorescence Detection

In an especially preferred embodiment of the invention, SPB in food, particularly fish, products are detected and enumerated using manual or automatic a fluorescence measurement techniques.

Portions of an incubation mixture containing the stomached fish or fish (or food) product are incubated at a predetermined temperature, preferably 30° C.±0.5° C. and fluorescence measurements are taken manually or automatically at predetermined intervals, for example, every 15, 30,45 or 60 minutes. Fluorescence measurements are continued to be taken at appropriate intervals at least until a peak (a maximum) in the level of fluorescence is detected. As noted earlier, the time until the fluorescence peak is attained is referred to as the "time to detection" (TTD) or "detection time". TTD generally occurs during the phase of incubation when the visible color of the incubation mixture changes from yellow to gray. Therefore, optimally, fluorescence measurements are especially preferred to be taken during the yellow-to-gray color change phase to ensure that the fluorescence peak (the fluorescence maximum) is detected.

As noted previously, the results shown in FIGS. 1 and 2 indicate that when concentrations of SPB are initially high, the TTD occurs early during the incubation period, whereas when concentrations of SPB are low, the TTD occurs much later during the incubation period.

TTD can be used to provide a quantitative enumeration of SPB in the original sample of food or fish or fish product by comparing the TTD for a particular product to a previously formulated correlation schedule, such as shown in FIG. 3 for cod, coal fish, wolf fish and salmon. It is well within the ability of a person of ordinary skill in the art, given the teachings herein, to formulate a correlation schedule such as FIG. 3 or Table 1 which relates time to peak fluorescence (TTD) to concentration of SPB in the product.

In a preferred version of the invention for example, when the TTD is within about 10±0.5 hours, a fish sample is considered to have about $10^4$ CFU/g of SPB or more (Table 1). A level of $10^6$ CFU/g is generally considered to be the maximum level of SPB which can be present in a fish sample to be shipped in a fresh condition. When the TTD is within about 6±0.5 hours, the fish sample is considered to have at least $10^6$ CFU/g. When the TTD is greater than 6±0.5 hours, the fish sample is considered to have less than $10^6$ CFU/g.

Any such TTD or CFU/g threshold can be used in a "pass-fail" version of the present invention (for example, using the values in Table 1). For example, if the threshold is $10^4$ CFU/g, then the fish sample "fails" (i.e., has at least $10^4$ CFU/g) if the TTD is less than about 10±0.5 hours, and "passes" (i.e., has fewer than $10^4$ CFU/g) if the TTD is greater than about 10±0.5 hours. Similarly, if the threshold is $10^6$ CFU/g, then the fish sample "fails" (i.e., has at least $10^6$ CFU/g) if the TTD is less than about 6±0.5 hours, and "passes" (i.e., has fewer than $10^6$ CFU/g) if the TTD is greater than about 6±0.5 hours. "Pass-fail" thresholds which have more narrow TTD ranges can be easily calculated for each testing site based on specific types of food products desired to be tested and testing procedures and facilities at each site.

TABLE 1

| Detection Time (hr) | Number of SPB (CFU/g) |
| --- | --- |
| 4 ± .5 | $10^7$ |
| 5 ± .5 | $5 \times 10^6$ |
| 6 ± .5 | $10^6$ |
| 7 ± .5 | $5 \times 10^5$ |
| 8 ± .5 | $10^5$ |
| 9 ± .5 | $5 \times 10^4$ |
| 10 ± .5 | $10^4$ |
| 11 ± .5 | $5 \times 10^3$ |
| 12 ± .5 | $10^3$ |
| 13 ± .5 | $10^2$ |
| 14 ± .5 | $5 \times 10^1$ |

Correlation of Detection Time (TTD) and Numbers of Sulfide-Producing Bacteria (CFU/g)

Visual Detection and Enumeration

In one embodiment of the present invention, sulfide-producing bacteria are detected and semi-quantitatively enumerated visually. In one embodiment, a sample of fish is prepared as previously described and is combined with a sterile iron broth as described above to form a sample-media mixture (an incubation mixture). The incubation mixture is then incubated at a predetermined incubation temperature such as 30° C., or another temperature as described elsewhere herein.

The color of the incubation mixture is assessed visually at intervals during the incubation period to determine at what time the sample changes color from yellow to gray (FIG. 4). The color of the incubation mixture at any particular incubation time can be matched with a correlation schedule such as a detection chart (Table 2, for example) to make a semi-quantitative determination of the concentration of sulfide-producing bacteria in the food sample at that time interval.

For example, using Table 2, if the incubation mixture is still yellow after up to about five hours of incubation, the original sample is considered to have less than about $10^6$ CFU/gm. If the color of the incubation mixture has changed from yellow to gray after up to about five hours, the original sample is considered to have about $10^6$ CFU/gm. If the color of the incubation mixture has changed to black after up to about five hours, the original sample is considered to have more than about $10^6$ CFU/gm.

If the color of the incubation mixture is still yellow after from about five up to about eight hours of incubation, the sample is considered to have less than about $10^5$ to $10^6$ CFU/gm. If the color of the incubation mixture has changed from yellow to gray after from about five up to about eight hours of incubation, the sample is considered to have about $10^5$ to $10^6$ CFU/gm. If the color of the incubation mixture has changed to black after from about five up to about eight hours of incubation, the sample is considered to have more than about $10^5$ to $10^6$ CFU/gm.

If the color of the incubation mixture is still yellow after from about eight up to about ten hours of incubation, the sample is considered to have less than about $10^4$ to $10^5$ CFU/gm. If the color of the incubation mixture has changed from yellow to gray after from about eight up to about ten hours of incubation, the sample is considered to have about $10^4$ to $10^5$ CFU/gm. If the color of the incubation mixture has changed to black after from about eight up to about ten hours of incubation, the sample is considered to have more than about $10^4$ to $10^5$ CFU/gm.

If the color of the incubation mixture is still yellow after from about ten up to about twelve hours of incubation, the sample is considered to have less than about $10^3$ to $10^4$ CFU/gm. If the color of the incubation mixture has changed from yellow to gray after from about ten up to about twelve hours of incubation, the sample is considered to have about $10^3$ to $10^4$ CFU/gm. If the color of the incubation mixture has changed to black after from about ten up to about twelve hours of incubation, the sample is considered to have more than about $10^3$ to $10^4$ CFU/gm.

If the color of the incubation mixture is still yellow after from twelve up to about fourteen hours of incubation, the sample is considered to have less than about $10^2$ to $10^3$ CFU/gm. If the color of the incubation mixture has changed from yellow to gray after from about twelve up to about fourteen hours of incubation, the sample is considered to have about $10^2$ to $10^3$ CFU/gm. If the color of the incubation mixture has changed to black after from about twelve up to about fourteen hours of incubation, the sample is considered to have more than about $10^2$ to $10^3$ CFU/gm.

If the incubation mixture is still yellow after about fourteen hours of incubation, the sample is considered to have less than about $10^2$ CFU/gm. If the color of the incubation mixture has changed from yellow to gray after about fourteen hours, the sample is considered to have about $10^2$ CFU/gm. If the color of the incubation mixture has changed to black after about fourteen hours, the sample is considered to have more than about $10^2$ CFU/gm.

It will be understood by those of ordinary skill in the art that when other conditions are used to incubate the incubation mixtures, for example using other incubation temperatures, or using other growth media, the concentrations and incubation times listed in Table 2 may be adjusted and the determination of such adjustments are considered to be well within the ability of a person of ordinary skill in the art using standard techniques.

TABLE 2

| INCUBATION TIME | COLOR OF MIXTURE | | |
|---|---|---|---|
| (hr) | YELLOW | GRAY | BLACK |
| $\leq 5$ | $\leq 10^6$ | $10^6$ | $>10^6$ |
| 5–8 | $\leq 10^5$–$10^6$ | $10^5$–$10^6$ | $>10^5$–$10^6$ |
| 8–10 | $\leq 10^4$–$10^5$ | $10^4$–$10^5$ | $>10^4$–$10^5$ |
| 10–12 | $\leq 10^3$–$10^4$ | $10^3$–$10^4$ | $>10^3$–$10^4$ |
| 12–14 | $\leq 10^2$–$10^3$ | $10^2$–$10^3$ | $>10^2$–$10^3$ |
| $14\geq$ | $\leq 10^2$ | $10^2$ | $>10^2$ |

Semi-Quantitative Enumeration of Sulfide-Producing Bacteria Approximate CFU/g for samples incubated in iron broth at 30° C.

In an alternative version of the visual detection and enumeration method, a portion of the food product sample to be tested is removed intact therefrom and is placed directly (without stomaching) into a container with the iron broth. For example, for each intact 2-gram portion, about 7 ml of iron broth medium is used. The medium with the intact portion is incubated in the same manner as the visual detection method described above. The color of the surface of the intact portion is observed at intervals as described elsewhere herein. The incubation time required to observe a darkening or blackening of a surface of the intact portion is then matched with a correlation schedule such as a detection chart (Table 3 for example) to make a semi-quantitative determination of the SPB in the original food sample.

For example, if the surface of the intact portion still has normal coloration after up to about five hours of incubation, the sample is considered to have less than about $10^6$ CFU/gm. If the color of the surface of the intact portion has changed to gray after up to about five hours, the sample is considered to have about $10^6$ CFU/gm. If the color of the surface of the intact portion has changed to black after up to about five hours, the sample is considered to have more than about $10^6$ CFU/gm.

If the color of the surface of the intact portion still has normal coloration after from about five up to about eight hours of incubation, the sample is considered to have less than about $10^5$ to $10^6$ CFU/gm. If the color of the surface of the intact portion has changed to gray after from about five up to about eight hours of incubation, the sample is considered to have about $10^5$ to $10^6$ CFU/gm. If the color of the surface of the intact portion has changed to black after from about five up to about eight hours of incubation, the sample is considered to have more than about $10^5$ to $10^6$ CFU/gm.

If the color of the surface of the intact portion still has normal coloration after from about eight to up to about ten hours of incubation, the sample is considered to have less than about $10^4$ to $10^5$ CFU/gm. If the color of the surface of the intact portion has changed to gray after from about eight up to about ten hours of incubation, the sample is considered to have about $10^4$ to $10^5$ CFU/gm. If the color of the surface of the intact portion has changed to black after from about eight up to about ten hours of incubation, the sample is considered to have more than about $10^4$ to $10^5$ CFU/gm.

If the color of the surface of the intact portion still has normal coloration after from about ten up to about twelve hours of incubation, the sample is considered to have less than about $10^3$ to $10^4$ CFU/gm. If the color of the surface of the intact portion has changed to gray after from about ten up to about twelve hours of incubation, the sample is considered to have about $10^3$ to $10^4$ CFU/gm. If the color of the surface of the intact portion has changed to black after from about ten up to about twelve hours of incubation, the sample is considered to have more than about $10^3$ to $10^4$ CFU/gm.

If the color of the surface of the intact portion still has normal coloration after from about twelve up to about fourteen hours of incubation, the sample is considered to have less than about $10^2$ to $1^3$ CFU/gm. If the color of the surface of the intact portion has changed to gray after from about twelve up to about fourteen hours of incubation, the sample is considered to have about $10^2$ to $10^3$ CFU/gm. If the color of the surface of the intact portion has changed to black after from about twelve up to about fourteen hours of incubation, the sample is considered to have more than about $10^2$ to $10^3$ CFU/gm.

If the color of the surface of the intact portion still has normal coloration after about fourteen hours of incubation, the sample is considered to have less than $10^2$ CFU/gm. If the color of the surface of the intact portion has changed to gray after about fourteen hours, the sample is considered to have about $10^2$ CFU/gm. If the color of the surface of the intact portion is still normally colored has changed to black after fourteen hours, the sample is considered to have more than about $10^2$ CFU/gm.

It will be understood by those of ordinary skill in the art that when other conditions are used to incubate the incubation mixtures, for example using other incubation temperatures, or using other growth media, the concentrations and incubation times listed in Table 3 may be adjusted and the determination of such adjustments are considered to be well within the ability of a person of ordinary skill in the art using standard techniques.

TABLE 3

| INCUBATION | SURFACE COLOR OF INTACT PORTION | | |
|---|---|---|---|
| TIME (hr) | UNCHANGED | GRAY | BLACK |
| $\leq 5$ | $\leq 10^6$ | $10^6$ | $>10^6$ |
| 5–8 | $\leq 10^5$–$10^6$ | $10^5$–$10^6$ | $>10^5$–$10^6$ |
| 8–10 | $\leq 10^4$–$10^5$ | $10^4$–$10^5$ | $>10^4$–$10^5$ |
| 10–12 | $\leq 10^3$–$10^4$ | $10^3$–$10^4$ | $>10^3$–$10^4$ |
| 12–14 | $\leq 10^2$–$10^3$ | $10^2$–$10^3$ | $>10^2$–$10^3$ |
| $14\geq$ | $\leq 10^2$ | $10^2$ | $>10^2$ |

Semi-Quantitative Enumeration of Sulfide-Producing Bacteria Approximate CFU/g for samples incubated at 30° C.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description. Such modifications are intended to fall within the scope of the appended claims.

What is claimed is:

1. A method of detecting and enumerating sulfide-producing bacteria in a food sample, comprising:

preparing the food sample as a liquified food sample;

forming an incubation mixture by combining the liquified food sample with a growth medium comprising iron and sulfur, and wherein an iron precipitate is formed in the incubation mixture when sulfide-producing bacteria act upon the iron and sulfur in the growth medium;

incubating the incubation mixture at an incubation temperature;

taking a plurality of fluorescence measurements from the incubation mixture during the incubation period to detect a fluorescence peak, the fluorescence peak comprising a fluorescence increase followed by a fluorescence decrease, the fluorescence decrease coinciding with an accumulation of the iron precipitate in the incubation mixture, wherein the period of time to the fluorescence peak comprises a detection time; and estimating the number of sulfide-producing bacteria in the food product by comparing the detection time to a correlation schedule.

2. The method of claim 1 wherein in the step of providing the food sample, the food sample is selected from the group comprising beef, lamb, pork, poultry, fish, shellfish, molluscs, marine animals, crustaceans, or any product derived therefrom.

3. The method of claim 1 wherein in the step of incubating the incubation mixture, the incubation temperature is from about 28° C.±0.5° C. to about 35° C.±0.5° C.

4. The method of claim 1 wherein in the step of incubating the incubation mixture, the incubation temperature is about 30° C.±0.5° C.

5. The method of claim 1 wherein in the step of incubating the incubation mixture, the incubation period is from about 4 hours to about 17 hours.

6. The method of claim 1 wherein in the step of forming an incubation mixture, the iron is provided as ferric citrate or ferrous sulfate.

7. The method of claim 1 wherein in the step of forming an incubation mixture, the sulfur is provided as cysteine and thiosulfate.

8. The method of claim 1 wherein in the step of taking a plurality of fluorescence measurements, the fluorescence measurements are taken manually.

9. The method of claim 1 wherein in the step of taking a plurality of fluorescence measurements, the fluorescence measurements are taken automatically.

10. The method of claim 1 wherein in the step of estimating the number of sulfide-producing bacteria, the detection time and the number of sulfide-producing bacteria which corresponds thereto is selected from Table 1, wherein Table 1 comprises:

| Detection Time (hr) | Number of SPB (CFU/g) |
|---|---|
| 4 ± .5 | $10^7$ |
| 5 ± .5 | $5 \times 10^6$ |
| 6 ± .5 | $10^6$ |
| 7 ± .5 | $5 \times 10^5$ |
| 8 ± .5 | $10^5$ |
| 9 ± .5 | $5 \times 10^4$ |
| 10 ± .5 | $10^4$ |
| 11 ± .5 | $5 \times 10^3$ |
| 12 ± .5 | $10^3$ |

-continued

| Detection Time (hr) | Number of SPB (CFU/g) |
|---|---|
| 13 ± .5 | $10^2$ |
| 14 ± .5 | $5 \times 10^1$. |

11. A method of detecting and enumerating sulfide-producing bacteria in a food sample, comprising:

preparing the food sample as a liquified food sample;

forming an incubation mixture by combining the liquified food sample with a growth medium comprising iron and sulfur, and wherein an iron precipitate is formed in the incubation mixture when sulfide-producing bacteria act upon the iron and the sulfur in the growth medium;

incubating the incubation mixture at an incubation temperature for a predetermined incubation period which produces a fluorescence peak when a particular number of sulfide-producing bacteria are present;

taking a plurality of fluorescence measurements from the incubation mixture during the predetermined incubation period; and concluding that the food sample has at least the particular number of sulfide-producing bacteria when a fluorescence peak is attained by the end of the predetermined incubation period, and that the food sample does not have the predetermined number of sulfide-producing bacteria when a fluorescence peak is not attained by the end of the predetermined incubation period.

12. The method of claim 11 wherein in the step of providing the food sample, the food sample is selected from the group comprising beef, lamb, pork, poultry, fish, shellfish, molluscs, marine animals, crustaceans, or any product derived therefrom.

13. The method of claim 11 wherein in the step of incubating the incubation mixture, the incubation temperature is from about 28° C.±0.5° C. to about 35° C.±0.5° C.

14. The method of claim 11 wherein in the step of incubating the incubation mixture, the incubation temperature is about 30° C.±0.5° C.

15. The method of claim 11 wherein in the step of incubating the incubation mixture, the predetermined incubation period is one of 4±0.5 hours, 5±0.5 hours, 6±0.5 hours, 7±0.5 hours, 8±0.5 hours, 9±0.5 hours, 10±0.5 hours, 11±0.5 hours, 12±0.5 hours, 13±0.5 hours and 14±0.5 hours.

16. The method of claim 11 wherein in the step of incubating the incubation mixture, the particular number of sulfide-producing bacteria is one of $10^2$ CFU/g, $10^3$ CFU/g, $10^4$ CFU/g, $10^5$ CFU/g, $10^6$ CFU/g, $10^7$ CFU/g and $10^8$ CFU/g.

17. The method of claim 11 wherein in the step of forming an incubation mixture, the iron is provided as ferric citrate or ferrous sulfate.

18. The method of claim 11 wherein in the step of forming an incubation mixture, the sulfur is provided as cysteine and thiosulfate.

19. The method of claim 11 wherein in the step of taking a plurality of fluorescence measurements, the fluorescence measurements are taken manually.

20. The method of claim 11 wherein in the step of taking a plurality of fluorescence measurements, the fluorescence measurements are taken automatically.

21. A method of detecting an enumerating sulfide-producing bacteria in a food sample, comprising:

preparing the food sample as a liquified food sample;

forming an incubation mixture by combining the liquified food sample with a growth medium having a color and comprising iron and sulfur, and wherein an iron precipitate is formed in the incubation mixture when sulfide-producing bacteria act upon the iron and sulfur in the growth medium;

incubating the incubation mixture at an incubation temperature;

determining a time to color change at which time the color of the incubation mixture changes from yellow to gray due to an accumulation of the iron precipitate in the incubation mixture; and estimating the number of sulfide-producing bacteria in the food sample by comparing the time to color change to a correlation schedule.

22. The method of claim 21 wherein in the step of providing the food sample, the food sample is selected from the group comprising beef, lamb, pork, poultry, fish, shellfish, molluscs, marine animals, crustaceans, or any product derived therefrom.

23. The method of claim 21 wherein in the step of incubating the incubation mixture, the incubation temperature is from about 28° C.±0.5° C. to about 35° C.±0.5° C.

24. The method of claim 21 wherein in the step of incubating the incubation mixture, the incubation temperature is about 30° C.±0.5° C.

25. The method of claim 21 wherein in the step of incubating the incubation mixture, the predetermined incubation period is one of 4±0.5 hours, 5±0.5 hours, 6±0.5 hours, 7±0.5 hours, 8±0.5 hours, 9±0.5 hours, 10±0.5 hours, 11±0.5 hours, 12±0.5 hours, 13±0.5 hours and 14±0.5 hours.

26. The method of claim 21 wherein in the step of incubating the incubation mixture, the particular number of sulfide-producing bacteria is one of $10^2$ CFU/g, $10^3$ CFU/g, $10^4$ CFU/g, $10^5$ CFU/g, $10^6$ CFU/g, $10^7$ CFU/g and $10^8$ CFU/g.

27. The method of claim 21 wherein in the step of forming an incubation mixture, the iron is provided as ferric citrate or ferrous sulfate.

28. The method of claim 21 wherein in the step of forming an incubation mixture, the sulfur is provided as cysteine and thiosulfate.

29. A method of detecting and enumerating sulfide-producing bacteria in a food sample, comprising:

providing a food sample having a normal coloration;

providing a growth medium comprising iron and sulfur and disposing the food sample into the growth medium forming an incubation mixture, and wherein an iron precipitate is formed on a surface of the food sample in the incubation mixture when sulfide-producing bacteria act upon the iron and sulfur in the growth medium;

incubating the incubation mixture at an incubation temperature;

determining a time to color change at which time the normal coloration of the food sample darkens due to accumulation of iron precipitate on the surface of the food sample; and estimating the number of sulfide-producing bacteria in the food sample by comparing the time to color change to a correlation schedule.

30. The method of claim 29 wherein in the step of providing the food sample, the food sample is selected from the group comprising beef, lamb, pork, poultry, fish, shellfish, molluscs, marine animals, crustaceans, or any product derived therefrom.

31. The method of claim 29 wherein in the step of incubating the incubation mixture, the incubation temperature is from about 28° C.±0.5° C. to about 35° C.±0.5° C.

32. The method of claim 29 wherein in the step of incubating the incubation mixture, the incubation temperature is about 30° C.±0.5° C.

33. The method of claim 29 wherein in the step of incubating the incubation mixture, the predetermined incubation period is one of 4±0.5 hours, 5±0.5 hours, 6±0.5 hours, 7±0.5 hours, 8±0.5 hours, 9±0.5 hours, 10±0.5 hours, 11±0.5 hours, 12±0.5 hours, 13±0.5 hours and 14±0.5 hours.

34. The method of claim 29 wherein in the step of incubating the incubation mixture, the particular number of sulfide-producing bacteria is one of $10^2$ CFU/g, $10^3$ CFU/g, $10^4$ CFU/g, $10^5$ CFU/g, $10^6$ CFU/g, $10^7$ CFU/g and $10^8$ CFU/g.

35. The method of claim 29 wherein in the step of forming an incubation mixture, the iron is provided as ferric citrate or ferrous sulfate.

36. The method of claim 29 wherein in the step of forming an incubation mixture, the sulfur is provided as cysteine and thiosulfate.

* * * * *